(12) United States Patent
Garner et al.

(10) Patent No.: US 8,461,978 B2
(45) Date of Patent: *Jun. 11, 2013

(54) WIRELESS ULTRASOUND PROBE ASSET TRACKING

(75) Inventors: David Garner, Roslindale, MA (US); Kevin Appareti, Methuen, MA (US); McKee Poland, Andover, MA (US); David Rust, Seattle, WA (US); Denise Marie Haley, New Bedford, MA (US); Martha Wilson, Andover, MA (US); Anthony Gades, Snohomish, WA (US); Christopher Fleming, Snohomish, WA (US); Dino Cuscuna, Reading, MA (US); John Fraser, Woodinville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 510 days.

This patent is subject to a terminal disclaimer.

(21) Appl. No.: 12/600,895

(22) PCT Filed: May 21, 2008

(86) PCT No.: PCT/IB2008/052005
§ 371 (c)(1),
(2), (4) Date: Jun. 9, 2010

(87) PCT Pub. No.: WO2008/146206
PCT Pub. Date: Dec. 4, 2008

(65) Prior Publication Data
US 2010/0277305 A1 Nov. 4, 2010

Related U.S. Application Data

(60) Provisional application No. 60/941,439, filed on Jun. 1, 2007.

(51) Int. Cl.
*G08B 1/08* (2006.01)

(52) U.S. Cl.
USPC ............. 340/539.1; 340/539.21; 340/568.1

(58) Field of Classification Search
USPC ............. 340/539.1, 539.15, 539.21, 573.1, 340/573.4, 568.1, 691.3, 693.5; 600/437
See application file for complete search history.

(56) References Cited

U.S. PATENT DOCUMENTS 4,785,291 A * 11/1988 Hawthorne ............. 340/573.4
6,708,879 B2    3/2004 Hunt
(Continued)

FOREIGN PATENT DOCUMENTS

| WO | 2000030540 A | 6/2000 |
| WO | 2004023245 A | 3/2004 |
| WO | 2007047929 A | 4/2007 |

*Primary Examiner* — Anh V La

(57) ABSTRACT

A wireless ultrasound probe has a probe case enclosing a transducer array, an acquisition circuit, a transceiver and a battery. The probe also includes a loudspeaker which produces audible sounds as a function of the range between the wireless probe and a host system. When the probe is within a near field range of the host system, the loudspeaker is silent. But if the probe is moved to an intermediate or a far field range from the host system, the loudspeaker sounds an alert. This audible alert can be used to locate the probe by transmitting a paging signal which, upon reception by the probe, causes the probe to sound its alert. If the probe is moved to an unauthorized location where it is within range of a transmitter or receiver, the reception of a signal by the probe, the transmitter, or receiver will sound an alert signaling the unauthorized presence of the wireless probe.

2 Claims, 16 Drawing Sheets

U.S. PATENT DOCUMENTS

| | | |
|---|---|---|
| 6,961,001 B1 * | 11/2005 | Chang et al. ............... 340/573.4 |
| 2002/0065464 A1 | 5/2002 | Murphy et al. |
| 2002/0158751 A1 | 10/2002 | Bormaster |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0112266 A1 | 5/2008 | Aoyama |
| 2008/0114239 A1 | 5/2008 | Randall et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0139944 A1 | 6/2008 | Weymer et al. |
| 2008/0161904 A1 | 7/2008 | Heuser et al. |
| 2008/0194961 A1 | 8/2008 | Randall |
| 2008/0194962 A1 | 8/2008 | Randall |
| 2008/0194963 A1 | 8/2008 | Randall |

* cited by examiner

WIRELESS ULTRASOUND PROBE ASSET TRACKING

This invention relates to medical diagnostic ultrasound systems and, in particular, to tracking and locating wireless ultrasound probes.

One of the long-time disadvantages of medical diagnostic ultrasound, particularly for sonographers, is the cable that connects the scanning probe to the ultrasound system. These cables are long and often thick due to the need to contain many coaxial lines from the dozens, hundreds, or even thousands of transducer elements in the probe. As a consequence, these probe cables can be cumbersome to deal with and can be heavy. Some sonographers try to deal with the cable problem by draping the cable over an arm or shoulder for support while scanning. This can lead to repetitive stress injuries in many cases. Another problem is that the probe cable can contaminate the sterile field of an image-guided surgical procedure. Furthermore, these probe cables are rather expensive, often being the most expensive component of the probe. Thus, there is a long-felt desire to rid diagnostic ultrasound of probe cables.

U.S. Pat. No. 6,142,946 (Hwang et al.) describes an ultrasound probe and system which do just that. This patent describes a battery-powered array transducer probe with an integral beamformer. A transceiver sends acquired ultrasound data to an ultrasound system serving as its base station. Image processing and display is done on the ultrasound system.

A wireless ultrasound probe provides excellent mobility, as it can be held and maneuvered in a variety of scanning positions without the need to manage a cable. However this mobility can also pose a hazard as the probe is no longer tethered to the ultrasound system. A wireless probe can be misplaced or lost in bedding in an examination room. A wireless probe can be easily carried to an unauthorized location including being carried from the medical facility by unauthorized personnel. Accordingly it is desirable to be able to locate a wireless probe when it is missing and have the probe sound or produce an alarm if the probe is being taken from a room or building without authorization.

In accordance with the principles of the present invention, a wireless ultrasound probe is provided which can be tracked and located electronically. The wireless probe includes a transceiver which communicates over a short range with a host system. Signal reception by either the probe transceiver or the host can be used as a range indication, based for instance on signal strength or transmit/receive timing, and an alarm sounded if the wireless probe and host become out of range with each other. The same transceiver ranging capability can be used with an auxiliary transmitter or receiver to detect when a wireless probe is being transported outside of an authorized area. The transceiver and onboard alert can be used to locate the probe by a paging technique.

Figure 2A:
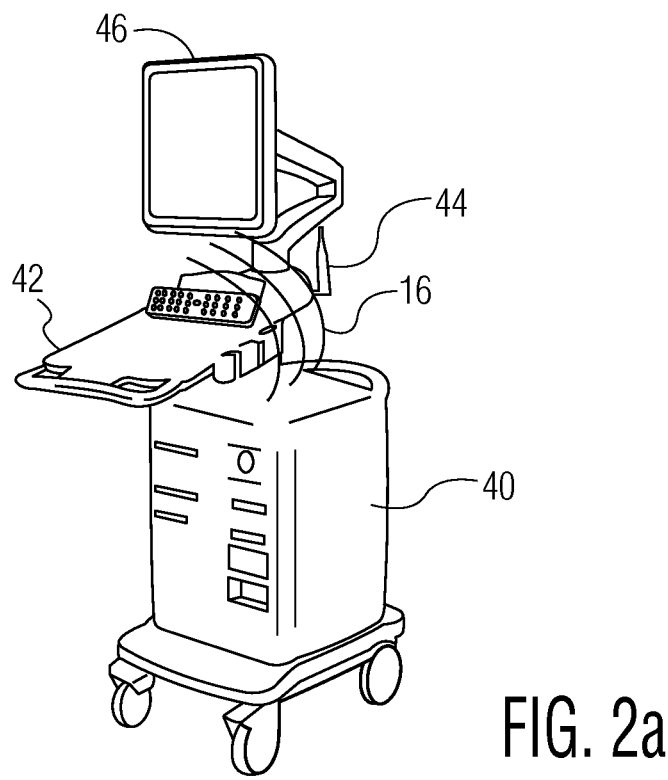
Figure 2B:
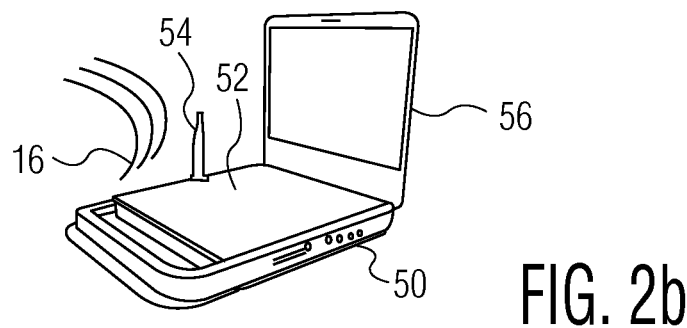
Figure 2C:
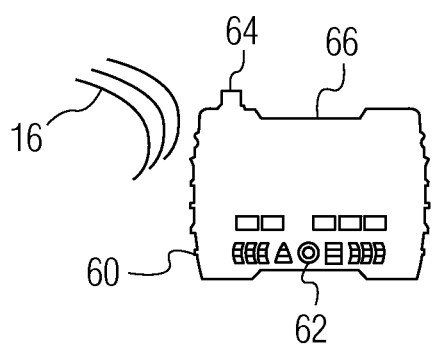

FIGS. 2a, 2b, and 2c illustrate different ultrasound display systems which may serve as base stations for a wireless probe of the present invention.

Figure 3:
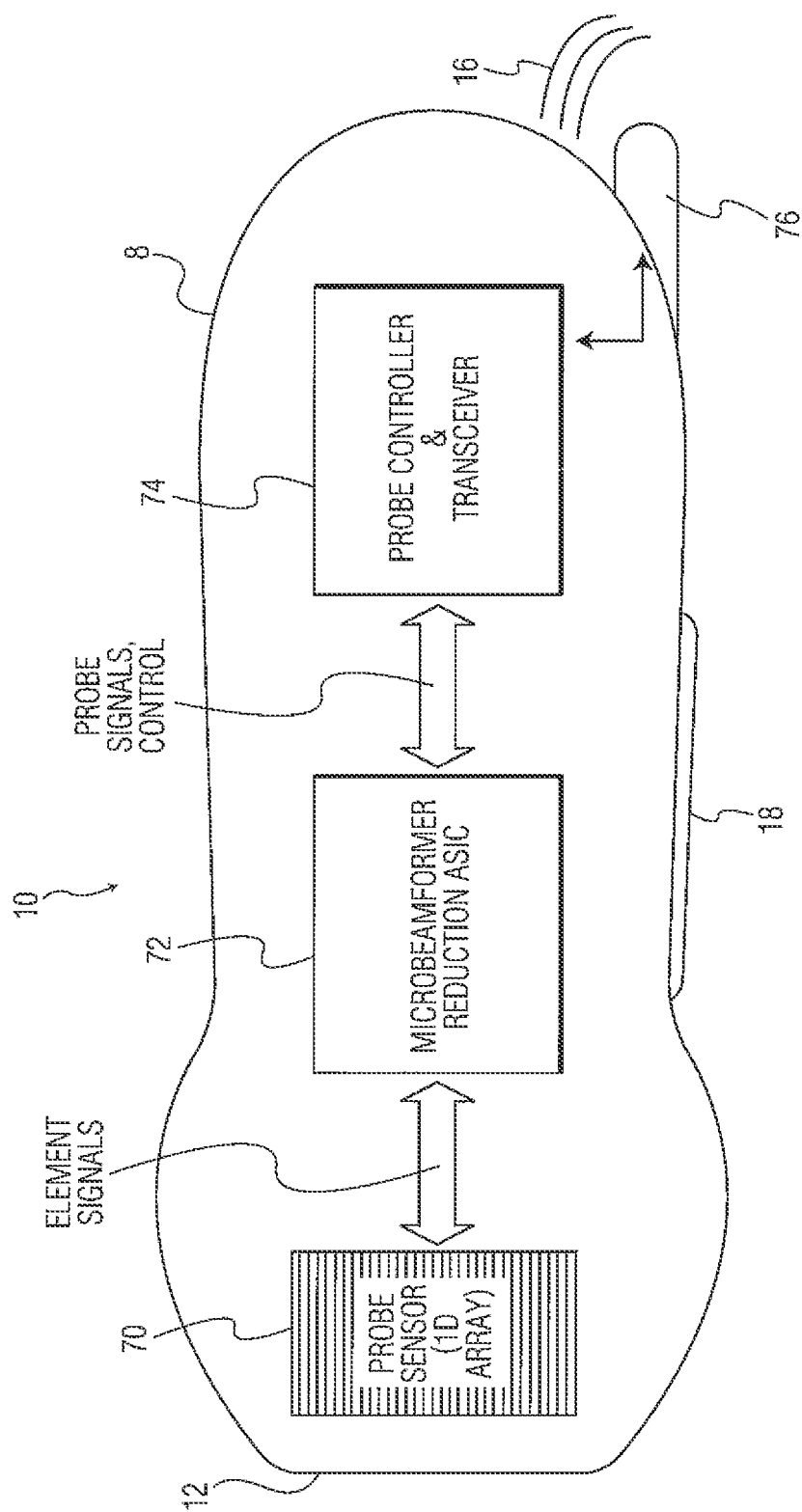

FIG. 3 illustrates the functional components of a wireless 1D array probe of the present invention.

Figure 4:
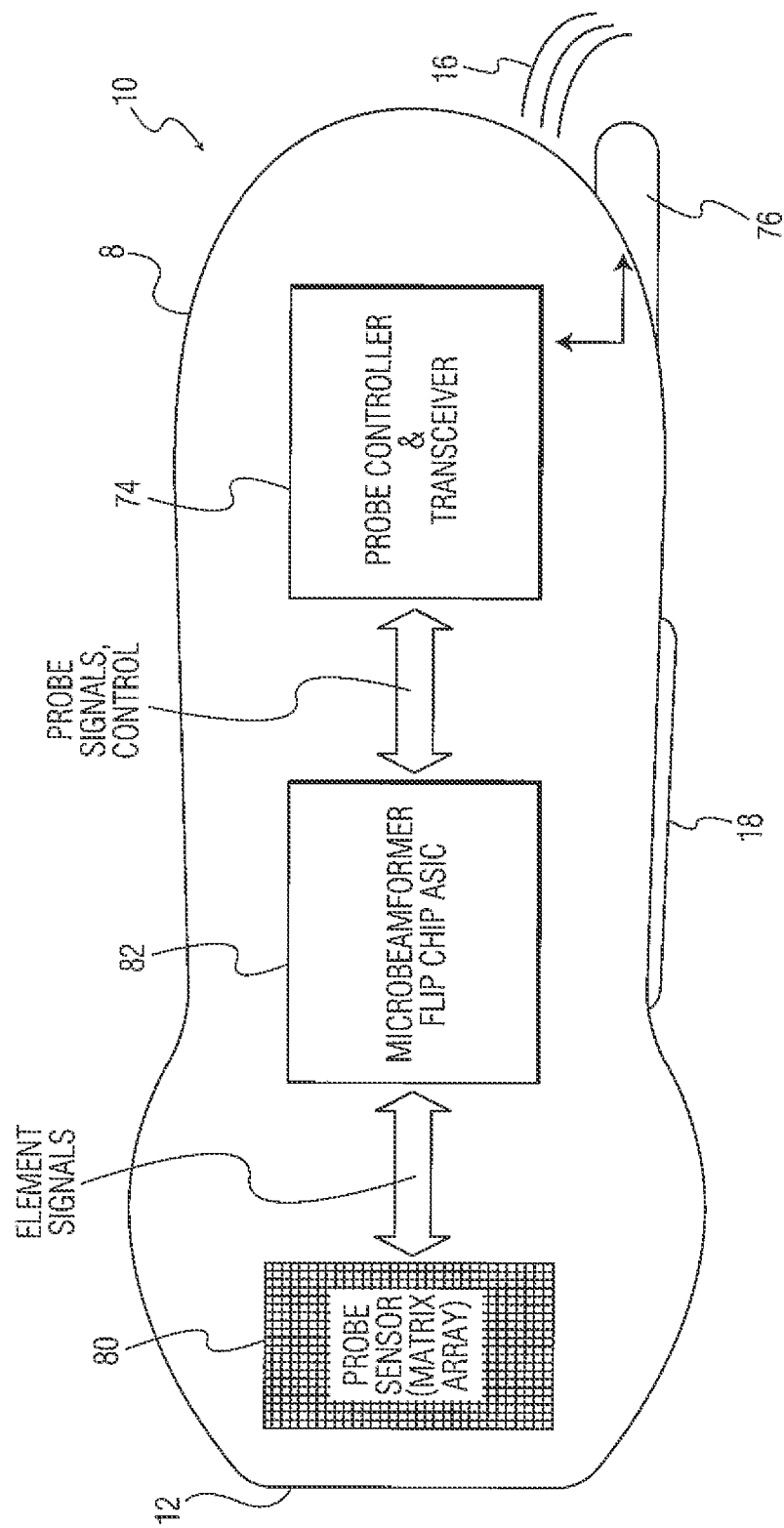

FIG. 4 illustrates the functional components of a wireless 2D array probe of the present invention.

Figure 5:
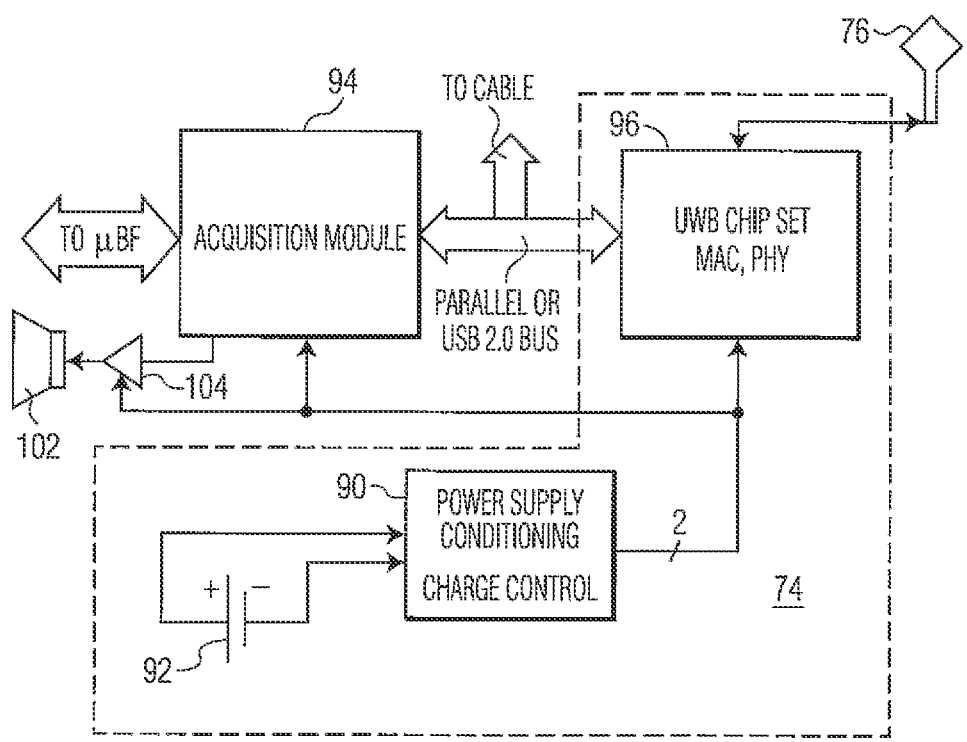

FIG. 5 illustrates in block diagram form the major electronic subsystems between the beamformer and antenna of a wireless probe of the present invention.

FIG. 6 illustrates in block diagram form the major components of a base station host for a wireless probe of the present invention.

Figure 7:
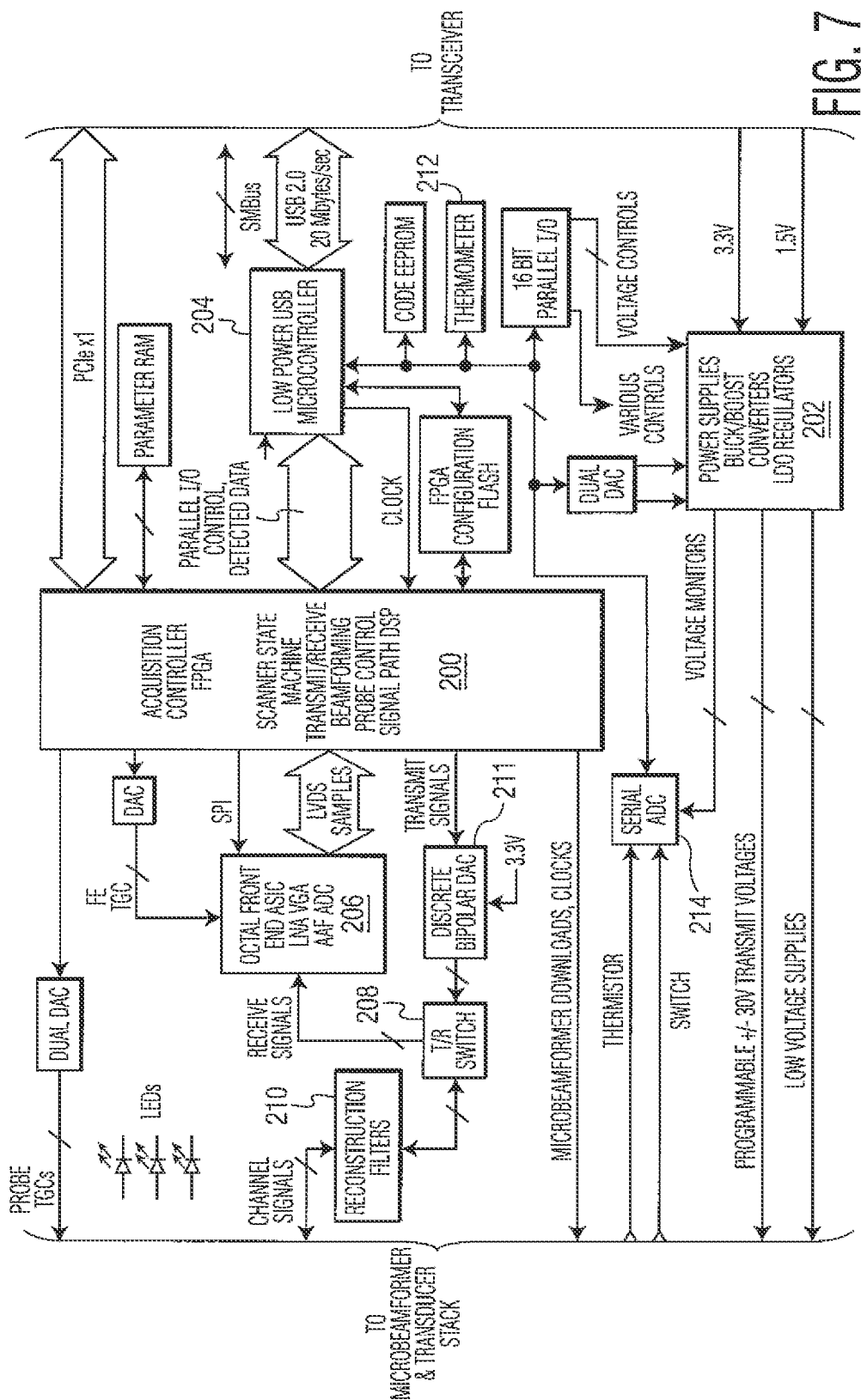

FIG. 7 illustrates in block diagram form an acquisition subsystem suitable for use in a wireless probe of the present invention.

Figure 8A:
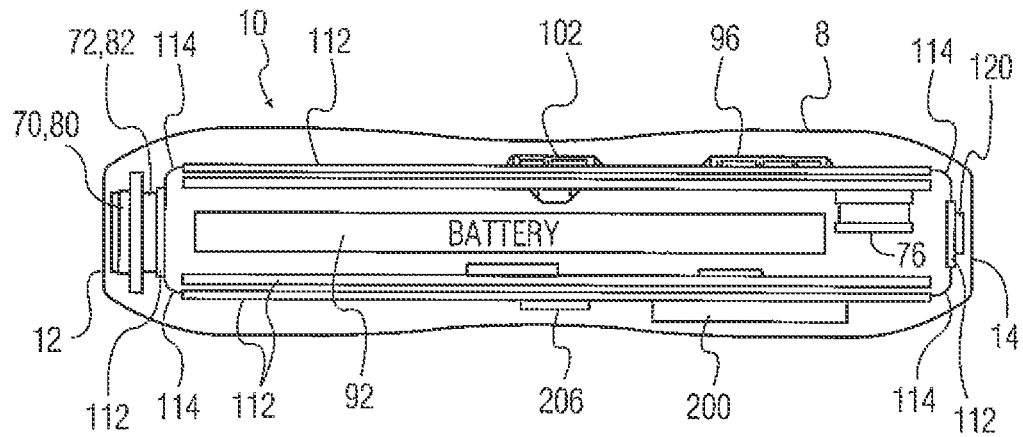
Figure 8B:
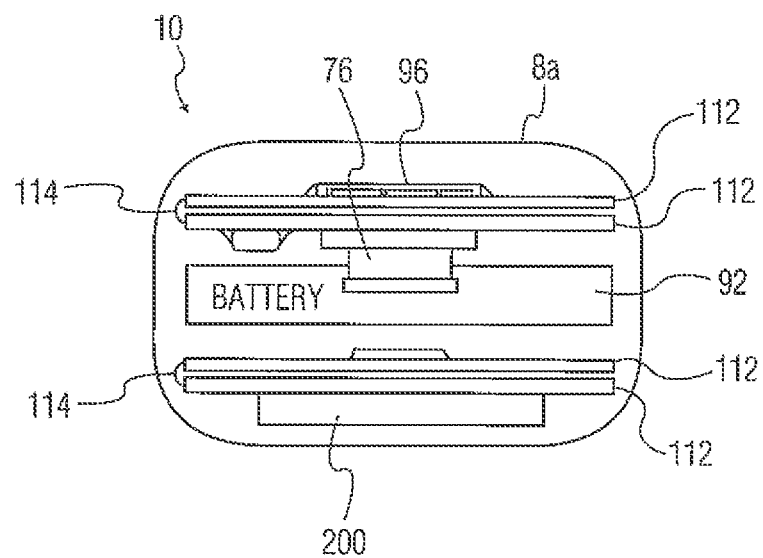

FIGS. 8a and 8b illustrate in cross-sectional views a lightweight wireless probe of the present invention.

Figure 9A:
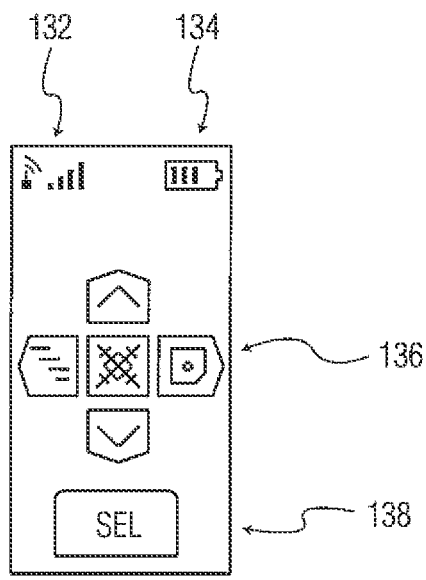
Figure 9B:
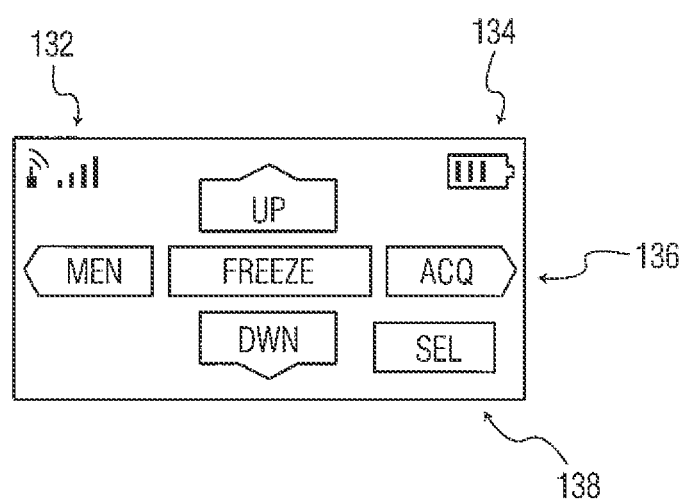

FIGS. 9a and 9b illustrate examples of a wireless probe user interface.

Figure 10A:
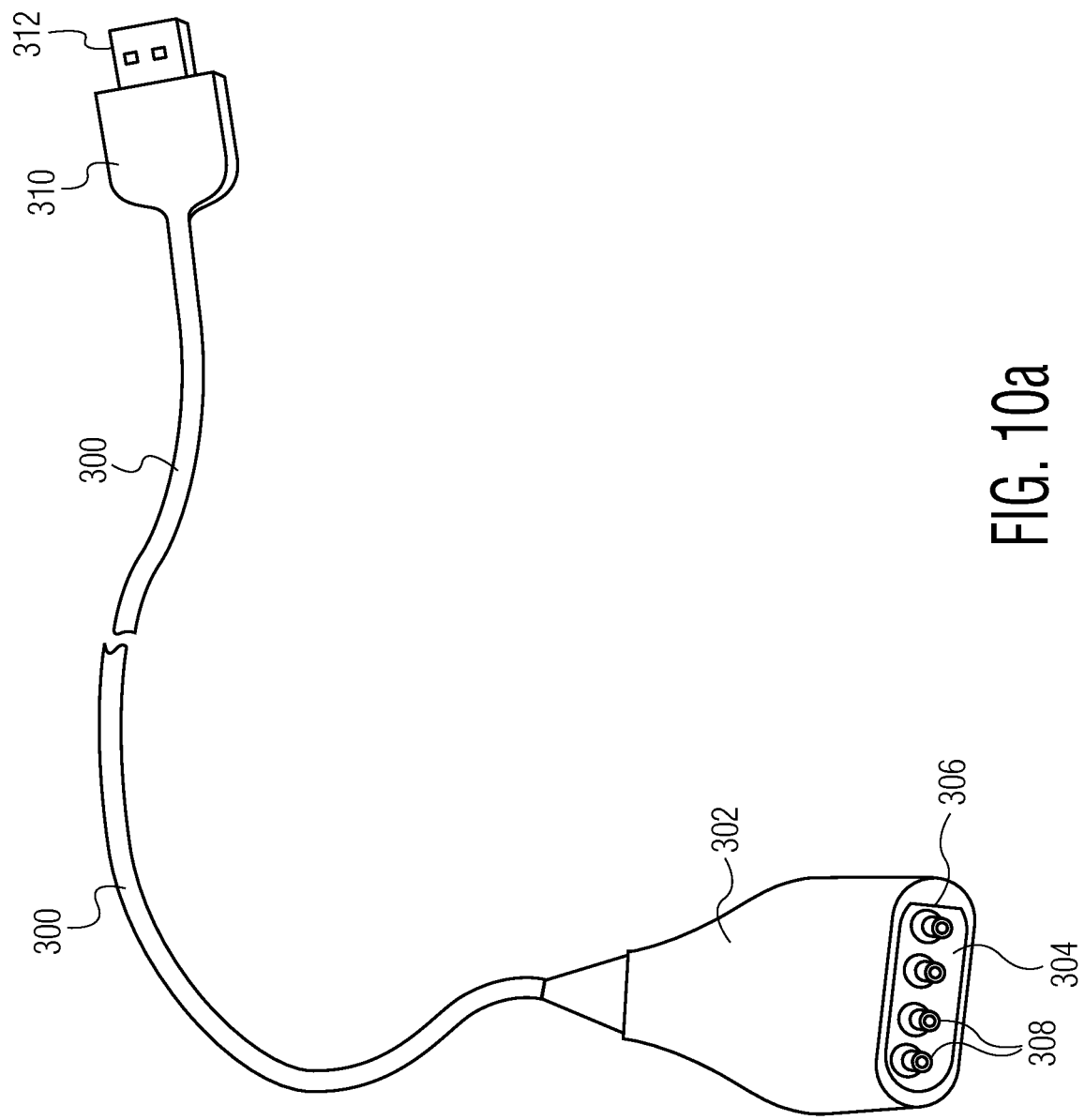
Figure 10B:
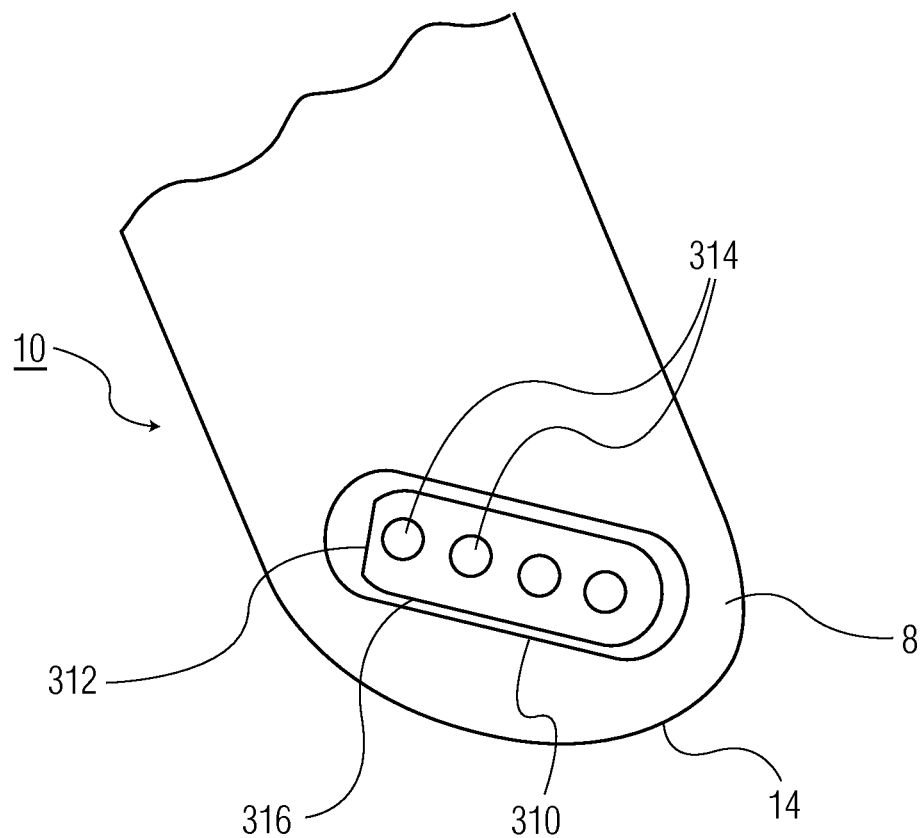

FIGS. 10a and 10b illustrate a USB cable for a wireless probe of the present invention.

Figure 11:
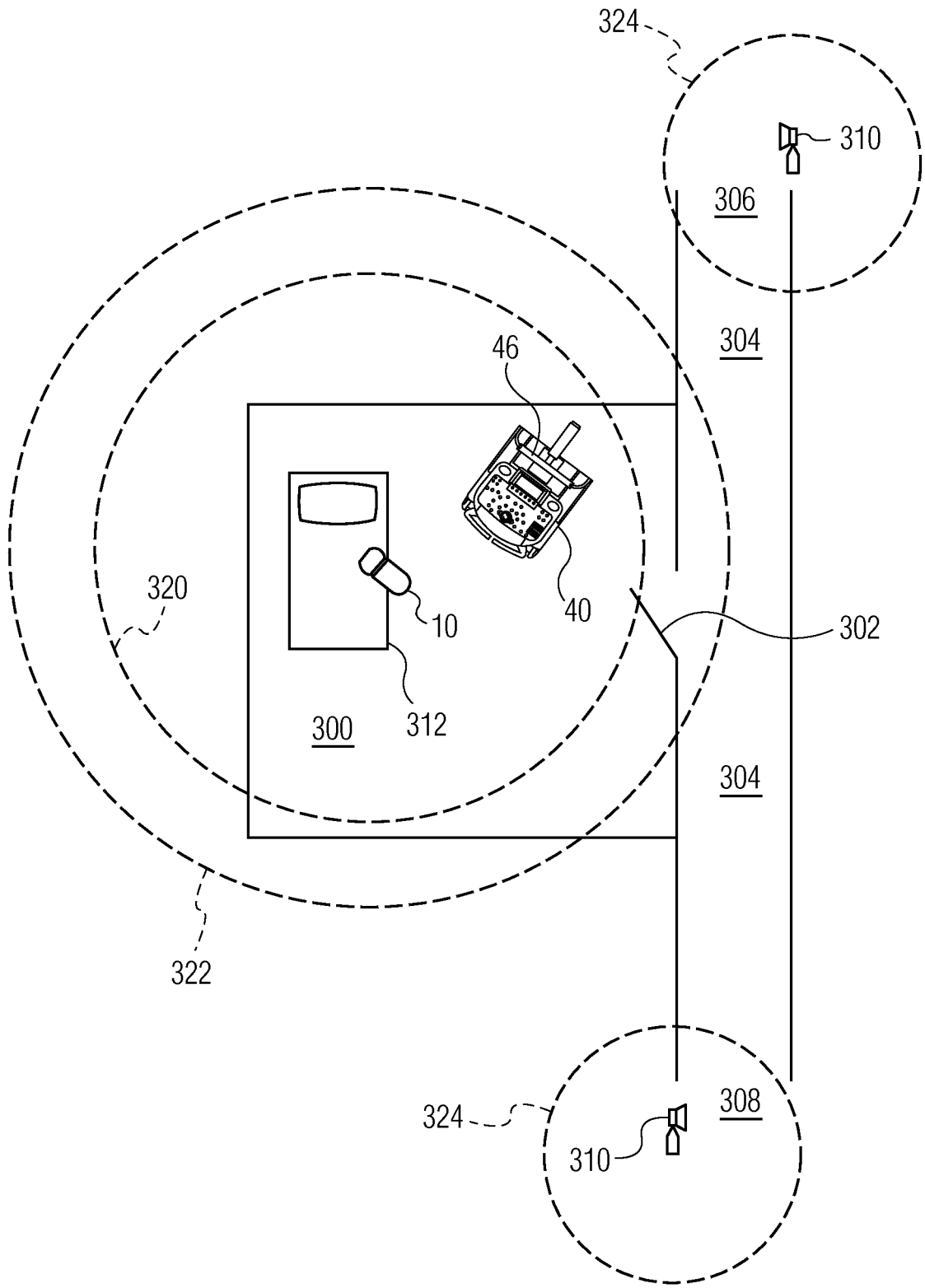

FIG. 11 illustrates the use of ranging for the detection and location of a wireless probe of the present invention.

Figure 12:
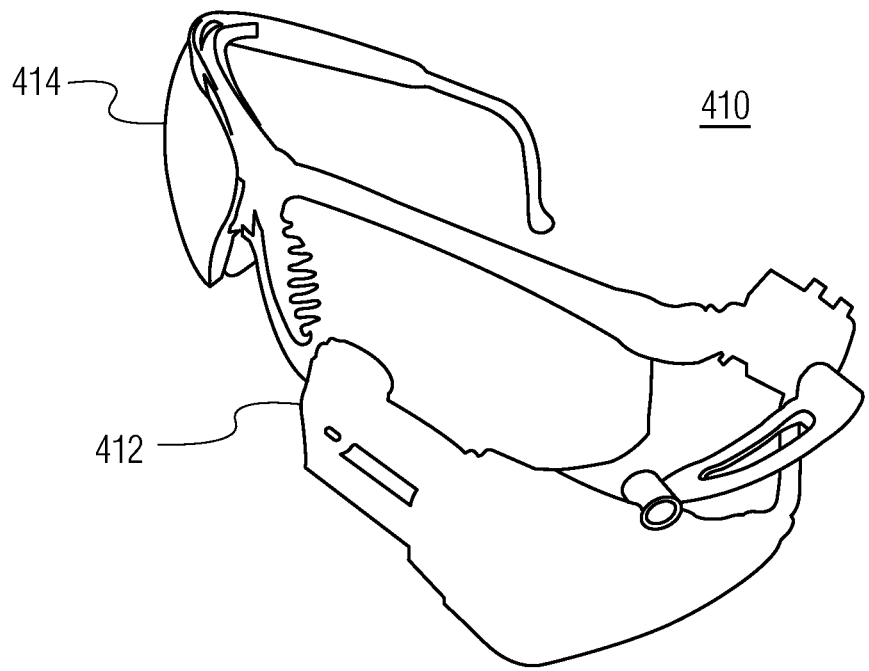

FIG. 12 illustrates a display headset accessory suitable for use with a wireless probe of the present invention.

Figure 13:
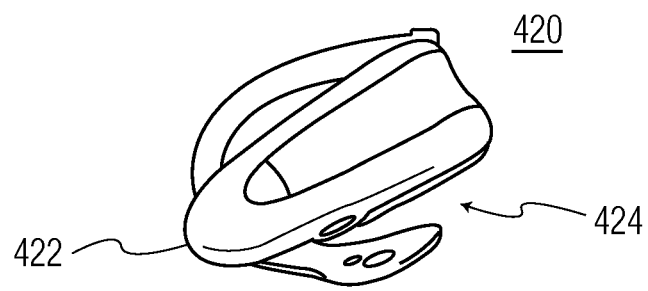

FIG. 13 illustrates a Bluetooth wireless voice transceiver accessory suitable for use with a wireless probe of the present invention.

Figure 14:
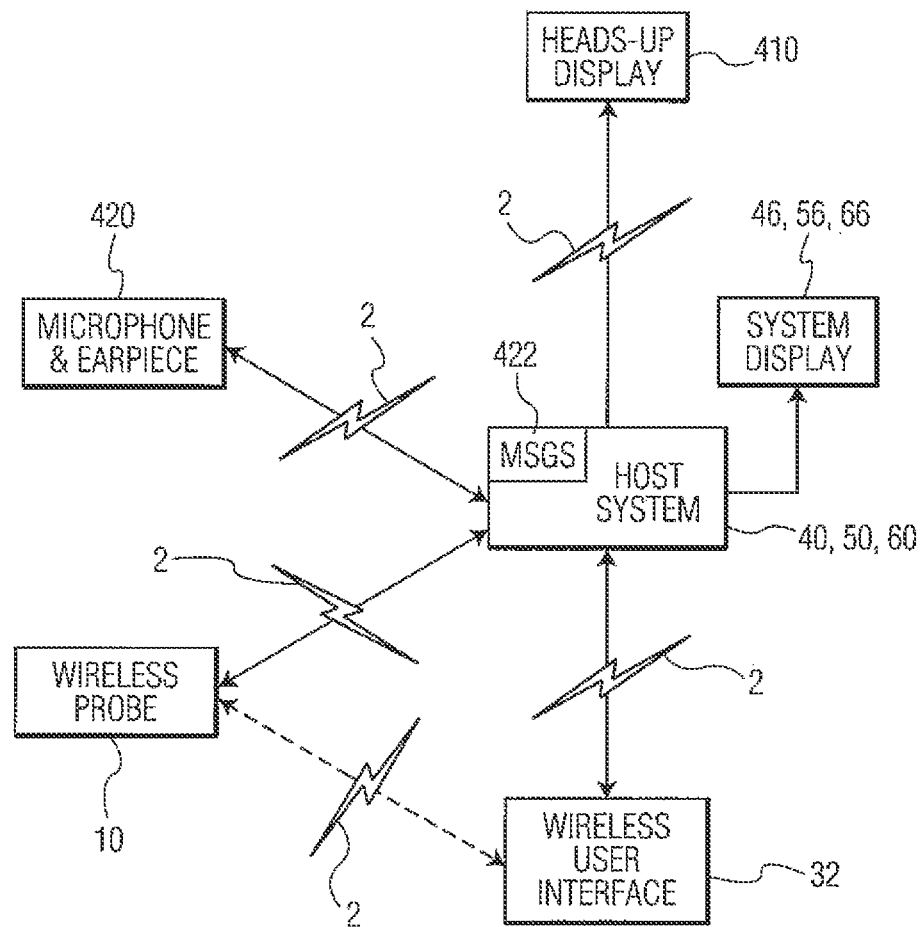

FIG. 14 illustrates a wireless probe of the present invention in use with a number of other wireless devices.

Figure 1A:
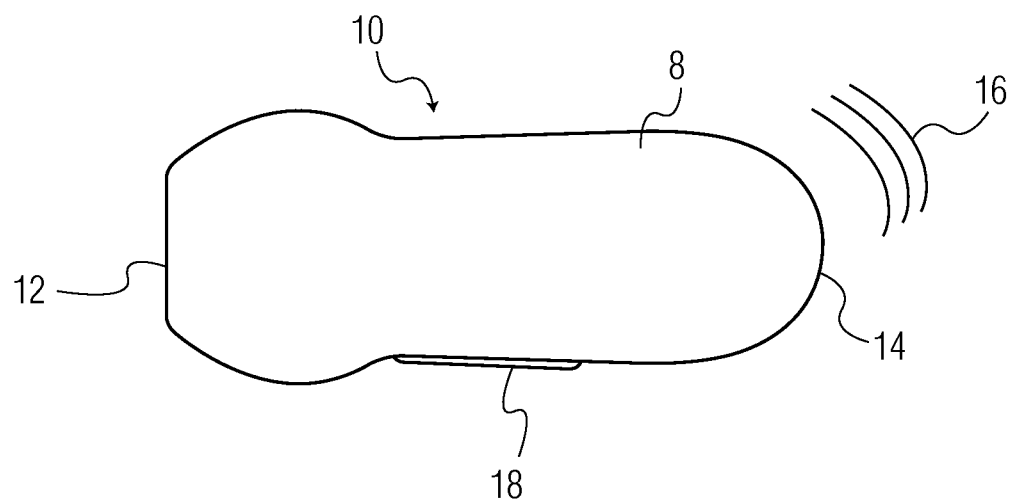
FIG. 1a illustrates a handheld wireless ultrasound probe of the present invention.

Referring first to FIG. 1, a wireless ultrasound probe 10 of the present invention is shown. The probe 10 is enclosed in a hard polymeric enclosure or case 8 which has a distal end 12 and a proximal end 14. The transducer lens or acoustic window 12 for the array transducer is at the distal end 12. It is through this acoustic window that ultrasound waves are transmitted by the transducer array and returning echo signals are received. An antenna is located inside the case at the proximal end 14 of the probe which transmits and receives radio waves 16 to and from a base station host. Battery charging contacts are also located at the proximal end of the probe as shown in FIGS. 10a and 10b. At the side of the probe 10 is a conventional left-right marker 18 which denotes the side of the probe corresponding to the left or right side of the image. See U.S. Pat. No. 5,255,682 (Pawluskiewicz et al.) The proximal portion of the body of the probe is seen to be narrower than the wider distal end of the probe. This is conventionally done so that the user can grasp the narrower proximal end and exert force against the expanded distal end when particularly firm contact with the skin of the patient is necessary. The probe case 8 is hermetically sealed so that it can be washed and wiped to remove gel and can be sterilized after use.

Figure 1B:
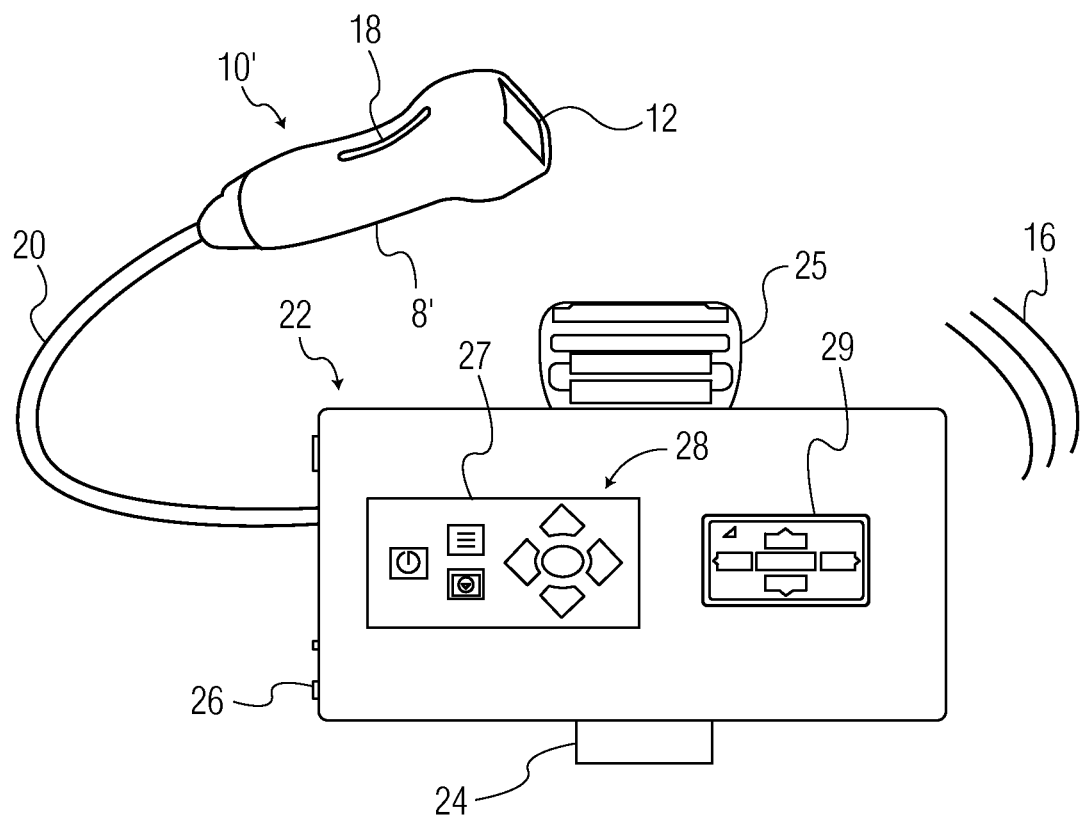
FIG. 1b illustrates a wireless ultrasound probe and attached user interface of the present invention.

FIG. 1b shows another example of a wireless probe 10' of the present invention which includes an attached transceiver user interface 22. The probe case 8' of this example contains the array transducer and may also include other components such as the beamformer and acquisition subsystem. However these other components may alternatively be located in the transceiver user interface 22, which has a size that accommodates user controls as shown on its top surface and discussed in conjunction with FIG. 1c. The controls are preferably implemented in a manner that permits easy cleanup in the ultrasound environment where gel is present, such as a sealed membrane or touchscreen display. The choice of location of the aforementioned other components will affect the cable 20 which connects the probe 10' with the user interface 22. If only the array transducer is located in the probe case 8', the cable 20 will include conductors for all of the array elements between the transducer array and the beamformer in the user interface 22. If the beamformer is located in the probe case 8', which is preferred, then the cable 20 can be thinner as the cable needs to conduct only beamformed or detected (and not per-element) signals and transducer power and control signals. See U.S. Pat. No. 6,102,863 (Pflugrath et al.) The cable 20 may be permanently connected to the user interface 22 but preferably is attached with a detachable connector so that the probe 10' can be separated cleaned, washed and sterilized or replaced with another probe.

In this embodiment the transceiver user interface 22 includes the radio transceiver and antenna that communicate with the base station host system. On the bottom of the user interface 22 is a wrist band or strap 24. This band or strap may be elastic or Velcro secured and goes around the forearm of the user. A right-handed user would thus wear the user interface 22 on top of the right forearm while holding the probe 10' in the right hand and operate the user controls on the right forearm with the left fingers.

Figure 1C:
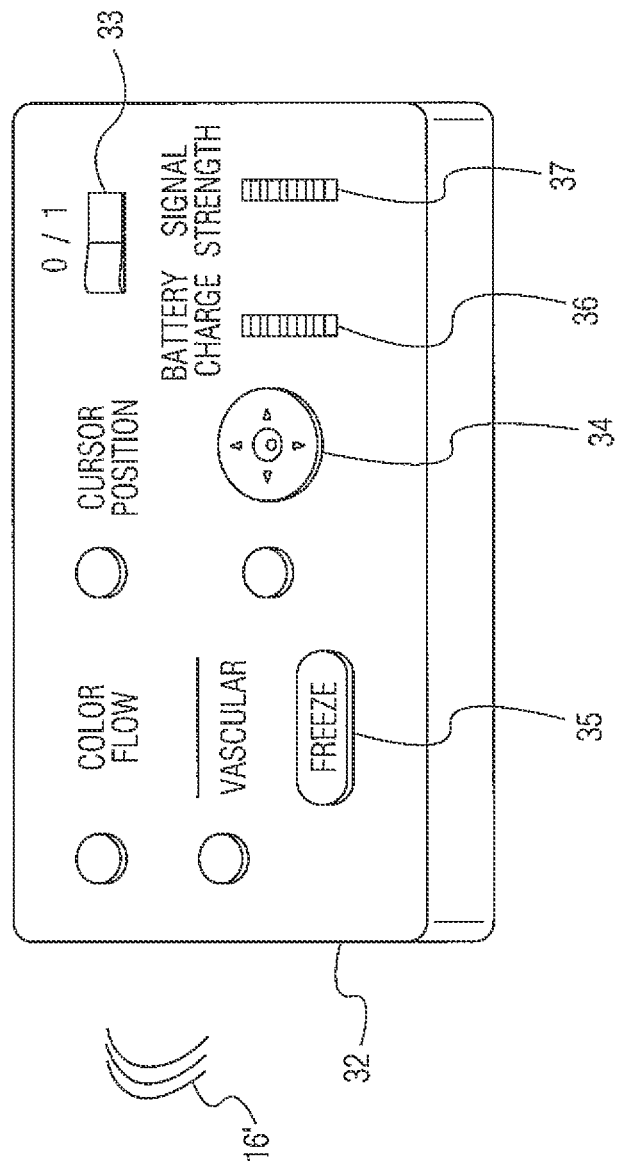
FIG. 1c illustrates a wireless user interface for a wireless probe of the present invention.

FIG. 1c shows a wireless user interface 32 for a wireless probe of the present invention. While the wireless probe 10 may if desired have a few simple controls on it as discussed below, many users will prefer to have the user controls entirely separate from the wireless probe. In such case the wireless probe 10 may have only an on/off switch or no controls at all, and the user controls for operating the probe can be the ultrasound system controls (42, see FIG. 2a) or the user controls of a wireless user interface 32. The example of a wireless user interface 32 in FIG. 1c contains a transmitter which transmits r.f. or infrared or other wireless control signals 16' either directly to the wireless probe 10 or to the base station host for subsequent relay to the wireless probe. In the illustrated example the user interface 32 is battery powered and includes an on/of switch 33 for the user interface and/or the wireless probe. Basic controls for a probe are also present such as a freeze button 35 and a rocker switch 34 to move a cursor. Other controls which may be present are mode controls and a select button. This example also includes a battery charge indicator 36 and a signal strength indicator 37 which indicate these parameters for the wireless probe 10, for the wireless user interface 32, or both. The wireless user interface can be operated while held in the user's hand or set on the bedside during a patient exam.

FIGS. 2a-2c illustrate examples of suitable base station host systems for a wireless ultrasound probe of the present invention. FIG. 2a illustrates a cart-borne ultrasound system 40 with a lower enclosure for system electronics and power supply. The system 40 has a control panel 42 which is used to control system operation and may be used to control the wireless probe. Controls on the control panel which may be used to control the probe include a trackball, select key, gain control knob, image freeze button, mode controls, and the like. Ultrasound images produced from signals received from the wireless probe are displayed on a display 46. In accordance with the principles of the present invention the cart-borne system 40 has one or more antennas 44 for the transmission and reception of signals 16 between the wireless probe and the host system. Other communication techniques besides r.f. signals may alternatively be employed such as an infrared data link between the probe and the system.

FIG. 2b illustrates a host system configured in a laptop computer form factor. The case 50 houses the electronics of the host system including the transceiver for communication with the wireless probe. The transceiver may be located inside the case 50, in an accessory bay of the case such as one for a media drive or battery. The transceiver may also be configured as a PCMCIA card or USB-connected accessory to the system as described in International Patent Publication WO 2006/111872 (Poland). Connected to the transceiver is one or more antennas 54. The wireless probe may be controlled from the control panel 52 of the system and the ultrasound images produced from the probe signals are displayed on a display 56.

FIG. 2c illustrates a battery-powered handheld display unit 60 suitable for use as a host system for a wireless probe of the present invention. The unit 60 has a ruggedized case designed for use in environments where physical handling is considerable such as an ambulance, emergency room, or EMT service. The unit 60 has controls 62 for operating the probe and the unit 60 and includes a transceiver which communicates by means of an antenna 64.

FIG. 3 illustrates a wireless probe 10 of the present invention constructed for two dimensional imaging. In order to scan a two dimensional image plane the probe 10 uses a one-dimensional (1D) transducer array 70 located at the distal end 12 of the probe at the acoustic window of the probe. The transducer array may be formed by ceramic piezoelectric transducer elements, a piezoelectric polymer (PVDF), or may be a semiconductor-based micromachined ultrasound transducer (MUT) such as a PMUT (piezoelectric MUT) or a CMUT (capacitive MUT) array of elements. The 1D array transducer 70 is driven by, and echoes are processed by, one or more microbeamformer reduction ASICs 72. The microbeamformer 72 receives echo signals from the elements of the 1D transducer array and delays and combines the per-element echo signals into a small number of partially beamformed signals. For instance the microbeamformer 72 can receive echo signals from 128 transducer elements and combine these signals to form eight partially beamformed signals, thereby reducing the number of signal paths from 128 to eight. The microbeamformer 72 can also be implemented to produce fully beamformed signals from all of the elements of the active aperture as described in the aforementioned U.S. Pat. No. 6,142,946. In a preferred embodiment fully beamformed and detected signals are produced by the probe for wireless transmission to the base station host so as to reduce the data rate to one which provides acceptable real time imaging. Microbeamformer technology suitable for use in beamformer 72 is described in U.S. Pat. No. 5,229,933 (Larson III); U.S. Pat. No. 6,375,617 (Fraser); and U.S. Pat. No. 5,997,479 (Savord et al.) The beamformed echo signals are coupled to a probe controller and transceiver subsystem 74 which transmits the beamformed signals to a host system, where they may undergo further beamforming and then image processing and display. The probe controller and transceiver subsystem 74 also receives control signals from the host system when the probe is controlled from the host, and couples corresponding control signals to the microbeamformer 72 to, for example, focus beams at a desired depth or transmit and receive signals of a desired mode (Doppler, B mode) to and from a desired region of an image. Not shown in this illustration are the power subsystem and battery to power the probe, which are described below.

The transceiver of the probe controller and transceiver subsystem 74 transmits and receives r.f. signals by means of a stub antenna 76, similar to that of a cellphone. The stub antenna provides one of the same benefits as it does on a cellphone, which is that its small profile makes it convenient to hold and carry and reduces the possibility of damage. However in this embodiment of a wireless probe, the stub antenna 76 serves an additional purpose. When a sonographer holds a conventional cabled probe, the probe is grasped from the side as if holding a thick pencil. A wireless probe such as that of FIG. 1a can be held in the same manner, however, since the probe has no cable, it can also be held by grasping the proximal end of the probe. This cannot be done with a conventional cabled probe due to the presence of the cable. A wireless probe user may want to hold the wireless probe by the proximal end in order to exert a large amount of force against the body for good acoustic contact. However, wrapping the hand around the proximal end of the probe, when the antenna is inside the proximal end of the probe, will shield the antenna from signal transmission and reception and may cause unreliable communication. It has been found that using an antenna which projects from the proximal end of the probe not only extends the antenna field well outside the probe case, but also discourages holding the probe by the proximal end due to the discomfort of pressing against the stub antenna. Instead, the user is more likely to grasp the probe from the side in the conventional manner, leaving the antenna field exposed for good signal transmission and reception. For good reception the antenna configuration of the base station host can introduce some diversity against polarization and orientation effects by producing two complementary beam patterns with different polarizations. Alternatively, the antenna can be a single high performance dipole antenna with a good single polarization beam pattern. With the antenna at the proximal end of the probe, the probe beam pattern can extend radially with respect to the longitudinal axis of the probe, and readily intersect the beam pattern of the base station host. Such a probe beam pattern can be effective with antennas of the base station host located at the ceiling, as may be done in a surgical suite. Reception has also be found to be effective with this probe beam pattern from reflections by room walls and other surfaces, which are often close to the site of the ultrasound exam. Typically a ten meter range is sufficient for most exams, as the probe and base station host are in close proximity to each other. Communication frequencies employed can be in the 4 GHz range, and suitable polymers for the probe case such as ABS are relatively transparent to r.f. signals at these frequencies. R.f. communication can be improved at the base station host, where multiple antennae can be employed for improved diversity in embodiments where multiple antennae are not cumbersome as they would be for the wireless probe. See, for example, International Patent Publication WO 2004/051882, entitled "Delay Diversity In A Wireless Communications System." The multiple antennae can utilize different polarizations and locations to provide reliable communications even with the varying linear and angular orientations assumed by the probe during the typical ultrasound exam. The typical probe manipulation can roll the probe throughout a 360° range of rotation and tilt angles through approximately a hemispherical range of angles centered on vertical. Hence, a dipole radiation pattern centered on the center longitudinal axis of the probe will be optimal for a single antenna and a location at the proximal end has been found to be most desirable. The antenna pattern can be aligned exactly with this center axis, or offset but still in approximate parallel alignment with this center axis.

FIG. 4 is another example of a wireless probe 10 of the present invention. In this example the wireless probe contains a two-dimensional matrix array transducer 80 as the probe sensor, enabling both two- and three-dimensional imaging. The 2D array transducer 80 is coupled to a microbeamformer 82 which is preferably implemented as a "flip chip" ASIC attached directly to the array transducer stack. As in the case of the wireless probe of FIG. 3, fully beamformed and detected echo signals and probe control signals are coupled between the microbeamformer and the probe controller and transceiver subsystem 74.

A typical probe controller and transceiver subsystem for a wireless probe of the present invention is shown in FIG. 5. A battery 92 powers the wireless probe and is coupled to a power supply and conditioning circuit 90. The power supply and conditioning circuit translates the battery voltage into a number of voltages required by the components of the wireless probe including the transducer array. A typical constructed probe may require nine different voltages, for example. The power supply and conditioning circuit also provides charge control during the recharging of the battery 92. In a constructed embodiment the battery is a lithium polymer battery which is prismatic and can be formed in a suitable shape for the available battery space inside the probe case.

An acquisition module 94 provides communication between the microbeamformer and the transceiver. The acquisition module provides timing and control signals to the microbeamformer, directing the transmission of ultrasound waves and receiving at least partially beamformed echo signals from the microbeamformer, which are demodulated and detected (and optionally scan converted) and communicated to the transceiver 96 for transmission to the base station host. A detailed block diagram of a suitable acquisition module is shown in FIG. 7. In this example the acquisition module communicates with the transceiver over a parallel or a USB bus so that a USB cable can be used when desired, as described below. If a USB or other bus is employed, it can provide an alternative wired connection to the base station host over a cable, thus bypassing the transceiver portion 96 as described below.

Also coupled to the acquisition module 94 and powered by the power supply and conditioning circuit 90 is a loudspeaker 102, driven by an amplifier 104, which produces audible tones or sounds. In a preferred embodiment the loudspeaker 102 is a piezoelectric loudspeaker located inside the case 8 and which may be behind a membrane or the wall of the case for good acoustics and sealing. The loudspeaker can be used to produce a variety of sounds or tones or even voice messages. The loudspeaker has a variety of uses. If the wireless probe is moved too far away from the host so that there is unreliable reception or even a complete loss of signal by the host or the probe, the loudspeaker can beep to alert the user. The loudspeaker can beep when the battery charge is low. The loudspeaker can emit a tone when the user presses a button or control on the probe, providing audible feedback of control activation. The loudspeaker can provide haptic feedback based upon the ultrasound examination. The loudspeaker can emit a sound when a paging control is activated to locate the probe. The loudspeaker can produce audio Doppler sounds during a Doppler exam, or heart sounds when the probe is used as an audio stethoscope.

The transceiver in this example is an ultra wideband chip set 96. The ultra wideband transceiver was found to have a data communication rate which provides acceptable real time imaging frame rates as well as acceptable range for an acceptable level of battery power consumption. Ultra wideband chip sets are available from a variety of sources such as General Atomics of San Diego, Calif.; WiQuest of Allen, Tex.; Sigma Designs of Milpitas, Calif.; Focus Semiconductor of Hillsboro, Oreg.; Alereon of Austin, Tex.; and Wisair of Campbell, Calif.

Figure 6A:
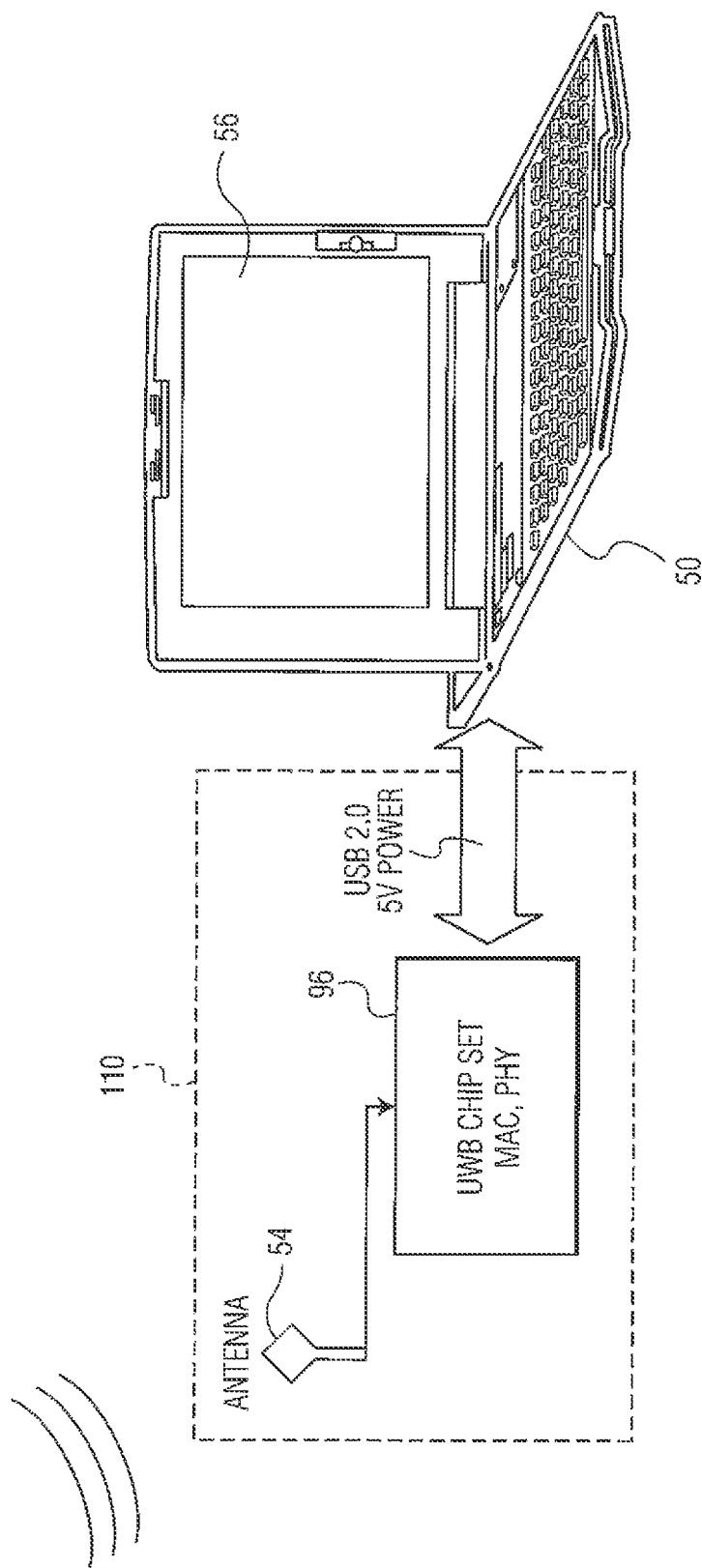
Figure 6B:
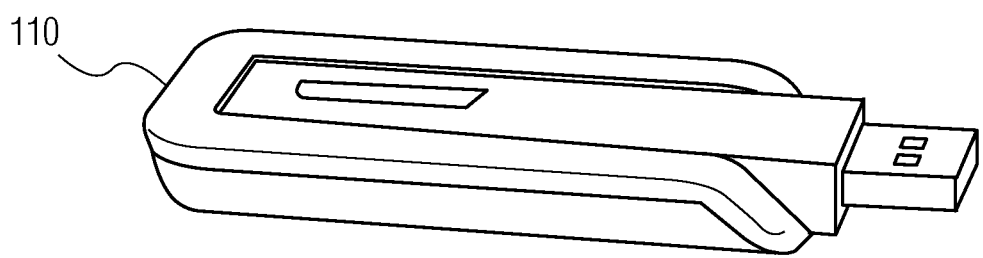

FIG. 6a illustrates the wireless probe signal path at the base station host, here shown in the laptop configuration 50. The antenna 54 is coupled to an identical or compatible ultra wideband chip set 96 which performs transception at the host. In a preferred embodiment for the laptop configuration, the antenna 54 and ultra wideband chip set are configured as a USB-connectible "dongle" 110 as shown in FIG. 6b, which plugs into and is powered by a USB port of the host system 50.

An example of an acquisition module suitable for use in a wireless probe of the present invention is shown in FIG. 7. At the left side of this drawing are signals coupled to and from the microbeamformer and the transducer array stack. This includes a stage of TGC signals, channel signals of beamformed echo signals from the microbeamformer, other data and clock signals for the microbeamformer, thermistor and switch signals to monitor overheating at the distal end of the probe, low voltage supplies for the microbeamformer and high voltages, in this example +/−30 volts, to drive the transducer elements of the array. At the right of the drawing are connections to the transceiver and, as described below, USB conductors and voltages from a USB conductor or the battery. These voltages supply power for power supplies, buck/boost converters for DC-DC conversion, and LDO regulators 202 which regulate the different voltage levels needed by the wireless unit including the acquisition subsystem and the transducer array drive voltage(s). This subsystem also monitors the battery voltage, which is sampled by a serial ADC 214 and the measured value used for a display of remaining battery power and to invoke power conservation measures as described below. The subsystem 202 shuts down the probe if the battery voltage approaches a level that would result in damage to the battery. It also monitors voltages consumed by the probe and acquisition electronics and similarly shuts them down if any approach unsafe levels.

At the heart of the acquisition module is an acquisition controller FPGA 200. This FPGA operates as a state machine to control the timing, mode and characteristics of ultrasound transmission and reception. The FPGA 200 also controls transmit and receive beamforming. The FPGA 200 contains a digital signal processor (DSP) which can be programmed to process received echo signals in various desired ways. Substantially all of the aspects of ultrasound transmission and reception are controlled by the FPGA 200. Received echo signals are coupled to the FPGA 200 by an octal front end ASIC 206. The ASIC 206 includes A/D converters to convert the received echo signals from the microbeamformer to digital signals. Variable gain amplifiers of the ASIC are used to apply a stage of TGC to the received echo signals. Received echo signals are filtered by reconstruction filters 210 and passed through a transmit/receive switch 208 to the front end ASIC 206. For ultrasound wave transmission transmit signals supplied by the FPGA 200 are converted to analog signals by a DAC 211, passed through the T/R switch 208, filtered by filters 210 and supplied to the microbeamformer for the array transducer.

In this implementation a low power USB microcontroller 204 is used to receive control information over a USB bus, which is communicated to the FPGA 200. Echo signals received and processed by the FPGA 200, preferably including demodulation and detection, are coupled to the microcontroller 204 for processing in USB format for a USB bus and the ultra wideband transceiver 96. These elements, including reconstruction filters 210, the T/R switch 208, the DAC 211 (on transmit), the front end ASIC 206 (on receive), the acquisition controller FPGA 200, and the USB microcontroller 204, comprise the ultrasound signal path between the transceiver 96 and the microbeamformer 72,82. The various other elements and registers shown in FIG. 7 will be readily understood by one skilled in the art.

FIGS. 8*a* and 8*b* illustrate the layout of a constructed wireless probe 10 of the present invention in longitudinal and transverse cross-sectional views. The components of the probe in this embodiment are located inside the case 8*a*. A space frame inside the case serves to mount and locate the components and also serves as a heat spreader to dissipate heat generated within the probe in a rapid and uniform manner. The electronic components of the probe are mounted on circuit boards 121 which are joined together by flex circuit connections 114. In this example the circuit boards and flex circuits form a continuous, unitary assembly for efficient and compact board interconnection and signal flow. As can be seen in FIG. 8*b*, the upper and lower parts of the electronic assembly each comprises two circuit boards 112 folded toward each other in parallel and connected by flex circuit 114. The front end ASIC 206 and the controller FPGA 200 can be seen mounted on the lower side of the lower circuit board in the drawings. The upper circuit boards in the probe mount power supply components and the transceiver chip set 96 with its antenna 76. In a particular implementation it may be desirable to use a separate circuit board for the ultra wideband chip set 96 which is specially designed for the high frequency components and signals of the transceiver. In the illustrated embodiment the piezoelectric loudspeaker 102 is located on the upper circuit board. Flex circuit 114 at the distal ends of the longitudinally extending circuit boards connect to a smaller circuit board 112 on which the microbeamformer chip(s) 72, 82 are located. Attached to the microbeamformer at the distal end 12 of the probe is the transducer array 70, 80.

In the illustrated assembly the battery 92 fills the center space of the probe between the circuit boards. The use of the illustrated lengthwise extending battery distributes the weight of the battery along most of the length of the probe and provides the probe with better balance when handled. The case can be fabricated with an opening so that the battery 92 can be accessed for replacement or the case can be sealed so that only factory replacement of the battery is feasible. Connected by flex circuit 114 at the proximal end of the probe case 8 is a small circuit board 112 on which a USB connector 120 is mounted. This connector can be a standard type A or type B USB connector. In a preferred embodiment the USB connector is configured as shown in FIGS. 10*a* and 10*b*.

The light-weight, compact design of FIGS. 8*a* and 8*b* distributes the weight of the probe components as follows. The case 8 and its space frame, the flex circuits 114, the transducer array 70, 80 and the microbeamformer 72, 82 weigh approximately 50 grams in a constructed embodiment. The acquisition module components 94, the ultra wideband chip set 96, the power supply and conditioning components 90 and the circuit boards for these components and chip set weigh approximately 40 grams. An 1800 mAH lithium polymer battery and connector weigh approximately 40 grams. The loudspeaker weighs about five grams and the antenna weighs about ten grams. A USB connector weighs about three grams. Thus, the total weight of this wireless probe is about 150 grams. With weight reduction possible for the space frame and circuit board assemblies, a weight of 130 grams or less can be attained. On the other hand, a larger battery for longer utilization between recharges, a larger aperture transducer array, and/or a bigger case for greater heat dissipation can double the weight to around 300 grams. While a smaller battery may provide scanning for an hour (one exam) before recharge, a larger battery could enable the wireless probe to be used all day (8 hours) and put in its cradle for recharge overnight. And some sonographers may want the lightest possible probe while others prefer a heavier probe with longer scanning duration between recharges. Depending upon the relative importance of these considerations for the designer and user, different probes of different weights can be realized.

In some implementations it may be desirable to produce a wireless probe which has no physical controls on it, as is the case for most conventional ultrasound probes today. Many sonographers will not want controls on a probe as it can be difficult to hold a probe in an imaging position with one hand while manipulating controls on the probe with the other hand, so-called cross-hand operation. In other implementations only an on/off switch is on the probe itself so the user can be assured that an unused probe is turned off and not depleting the battery. In still other implementations basic display information is found on the probe, such as signal strength and remaining battery life. Basic information of this sort on the probe will help a user diagnose a probe which is not operating properly. In yet other implementations some minimal controls may be desirable. With the user no longer tethered to the host system by a cable, the system controls conventionally used to operate the probe may no longer be within reach and minimal controls on the wireless probe itself can facilitate its independent operation. FIGS. 9a and 9b show two examples of information displays and controls which may be located on the body of the wireless probe. FIG. 9a illustrates a set of displays and controls arranged in a vertical orientation and graphically marked. FIG. 9b illustrates the same set of displays and controls arranged in a horizontal orientation and textually marked. A signal strength indicator 132 is displayed at the upper left and a battery charge indicator 134 is displayed at the upper right of each set of displays and controls. In the center is a set of controls which, in this example, include up and down arrows for setting gain, selecting a menu item or moving a cursor, a freeze control to freeze a frame of a live display on the screen, an acquire control to acquire and save a frozen image or live image loop, and a menu control to access a list of menu items for the probe. The up and down arrow controls are then used to navigate through the list of menu items and a select control 138 is used to select a desired menu item. These controls can be used to change the probe operating mode from B mode to color flow or to put a vector line or M-line over the image, for instance. The controls can be responsive to different actuation patterns for controlling multiple functions. For instance, holding down the menu and acquire controls simultaneously for three seconds can be used to turn the probe on or off, obviating the need for a separate on/off switch. Tapping the select control three times in rapid succession can cause the actuation of the controls and/or cause the display backlight to be illuminated. A special sequence to actuate the controls is desirable, since the user will often be pressing on the controls while holding and manipulating the wireless probe in normal scanning, and it is desirable to prevent normal manipulation of the probe from actuating a control when control actuation is not intended.

The audible capability of the loudspeaker or beeper 102 is preferably used to complement the display of visual information about the wireless probe and/or the actuation of controls. For instance, if the battery charge becomes low, the beeper can sound to alert the user to recharge the battery or use another probe. Another sound of the beeper can be used to alert the user to a low signal strength condition, and the user can move the base station host closer to the exam site or take care not to shield the antenna with a hand as discussed previously. The loudspeaker or beeper can produce a sound or vibration when a control is actuated, thereby providing feedback to the user that the actuation has taken place and been registered by the probe and/or system.

Various control and display technologies can be used for the wireless probe display and control layouts of FIGS. 9a and 9b. The controls can be simple mechanical contact switches covered with a sealing liquid-tight membrane with the control graphics printed on them. More preferably the displays and controls are touch-panel LED, LCD or OLED displays mounted on a circuit board 112 to be flush with the exterior surface of the case 8 and hermetically sealed for fluid-tightness to the surrounding case or visible through a window in the case. Touching a control display with a finger or special wand then actuates the selected touch-panel control function. See International Patent Publication WO 2006/038182 (Chenal et al.) and U.S. Pat. No. 6,579,237 (Knoblich).

While the major advantage of a wireless probe of the present invention is the elimination of the cumbersome cable and being tethered to the ultrasound system, there are situations in which a probe cable may be desirable. For example, a convenient way to recharge the battery of the wireless probe is to place the wireless probe in a charging cradle when the probe is not in use as shown in U.S. Pat. No. 6,117,085 (Picatti et al.) However it may be more convenient in some situations to use a cable to recharge the battery. A cable may be more portable than a charging cradle, for instance. Moreover, a cable with a standardized connector may enable recharging of the probe battery from a variety of common devices. In other situations, if a sonographer is conducting an ultrasound exam and the beeper sounds to indicate a low battery condition, the sonographer may want to continue using the probe to conduct the exam and may want to switch from battery power to cable power. In that situation a power cable would be desirable and the power subsystem 202 automatically switches to operation with cable power while the battery recharges. As yet another example, the r.f. or other wireless link to the base station host may be unreliable, as when electro-surgery equipment is being operated nearby or the sonographer needs to hold the probe with the antenna or other transmitter on the probe shielded from the host. In other situations the sonographer may desire a cable-connected probe so that the probe will not become separated from the system or will be suspended by the cable above the floor if dropped. There may be a situation where a cable provides improved performance, such as a greater bandwidth for transmission of diagnostics or upgrades of the probe's firmware or software. In other circumstances the probe may not pair successfully with the host system and only a wired connection will work. In such situations a cable for power, data communication, or both may be desired.

FIG. 10a illustrates a cable suitable for use with a wireless probe of the present invention. While various types of multi-conductor cables and connectors can be used for a wireless probe, this example is a multi-conductor USB cable 300 with a USB type A connector 310 at one end. Extending from the connector 310 is a type A USB adapter 312. Other USB formats may alternatively be employed, such as type B and mini-B as is found on digital cameras, or a completely custom connector with other desirable properties may be employed. A USB cable can be plugged into virtually any desktop or laptop computer, enabling the wireless probe to be charged from virtually any computer. When the host system is a laptop-style ultrasound system 50 as shown in FIGS. 2b and 6a, the USB-type cable can be used for both signal communication to and from the host as well as power.

The same style of USB connector can be provided at the other end of the cable 300 for connection to the wireless probe, in which case the wireless probe has a mating USB connector. The probe connector can be recessed inside the case and covered by a watertight cap or other liquid-tight removable seal when not in use. In the illustrated example the connector 302 to the probe contains four USB conductors 308. The conductors 308 are spring-loaded so they will press with good contact against mating conductors on the wireless probe. The conductors 308 are located on a recessed or projecting connector end piece 304 which is keyed at one end 306 to require mating with the probe in only one orientation.

A mating wireless probe 10 for the cable of FIG. 10a is shown in FIG. 10b. The connector 310 of the probe in this example is at the proximal end 14 and is completely hermetically sealed. The probe contacts 314 of the connector 310 are located in a recessed or projecting area 316 which mates with the projecting or recessed end piece 304 of the cable, and is similarly keyed at 312 for proper connection. When the cable connector 302 is plugged into the mating area 316 of the probe, the spring-loaded conductors 308 of the cable bear against the probe contacts 314 of the probe, completing the USB connection with the probe.

In accordance with the principles of a further aspect of the probe and cable of FIGS. 10a and 10b, the mating area 316 of the probe is not projecting or recessed but is flush with the surrounding probe surface. The mating area 316 is made of a magnetic or ferrous material which surrounds the contacts 314 and is magnetically attractive. The mating end piece 304 of the cable connector 302 similarly does not need to be projecting or recessed, but can also be flush with the end of the connector 302 and is made of a magnetized material which attracts to the mating area 316 of the probe. The magnetized material of the end piece 304 can be permanently magnetized or electro-magnetized so that it can be turned on and off. Thus, the cable is not connected to the probe by a physically engaging plug, but by magnetic attraction which can provide both keying (by polarity) and self-seating. This provides several advantages for a wireless probe. One is that the connector 310 of the probe does not have to have projections and recesses that can trap gel and other contaminants which are difficult to clean and remove. The connector 310 can be a smoothly continuous surface of probe case 8, mating area 316, and contacts 314 which is easy to clean and does not trap contaminants. The same advantage applies to the cable connector 302. The magnetic rather than physical connection means that the connection can be physically broken without damaging the probe. A sonographer who is used to using a wireless probe can become accustomed to the absence of a cable and can forget that the cable 300 is present when scanning. If the sonographer puts stress on the cable as by, for instance, running into it or tripping over it, the force will overcome the magnetic attraction connecting the cable to the probe and the cable 300 will break away harmlessly from the probe 10 without damaging it. Preferably the magnetic attraction is sufficiently strong to support the weight and momentum of the probe when hanging from the cable, which is aided by a wireless probe of 300 grams or less. Thus, if the cable-connected probe falls off of the examination table, it will be suspended by the magnetic cable and not fall loose and crash to the floor, saving the wireless probe from damage.

It will be appreciated that the cable may be a two-part device, with an adapter removably coupled to the probe and having a standardized connector for a cable. The adapter connects to a cable with a standardized connector such as a USB connector at both ends. In such a configuration the adapter can be used with any standardized cable of the desired length.

As with other battery-powered devices, power consumption is a concern in a wireless probe of the present invention. There are two reasons for this in a wireless probe. First, the wireless probe should desirably be able to image for an extended period of time before recharging is necessary. Second, heating is a concern for patient safety and component life, and a low thermal rise both at the transducer array and within the probe case 8 is desired. Several measures can be taken to improve power consumption and thermal characteristics of a wireless probe. One is that, whenever a charging cable is connected to the probe as discussed in conjunction with FIGS. 10a and 10b above, the probe should switch to using the supply voltage of the cable to operate the probe. While the battery may be charging at this time, it is desirable that battery power not be used to power the probe when a charging cable is connected. Another measure which can be taken is for the wireless probe to switch to a hibernate mode when the probe is not being used for imaging. See U.S. Pat. No. 6,527,719 (Olsson et al.) and International Patent Publication WO 2005/054259 (Poland). Several techniques can be used to automatically determine when the probe is not being used for imaging. One is to detect the reflection from the lens-air interface in front of the transducer array when the acoustic window of the probe is not in contact with a patient. See U.S. Pat. No. 5,517,994 (Burke et al.) and U.S. Pat. No. 5,654,509 (Miele et al.) Should this strong reflected signal persist for a predetermined number of seconds or minutes, the probe can assume that it is not being used for imaging and switch to a hibernate mode. Another technique is to periodically do Doppler scanning, even if not in a Doppler mode, to see if blood flow movement is detected, which is an indicator that the probe is in use. Speckle tracking and other image processing techniques can be used to detect motion. Still another approach is to mount one or more accelerometers inside the probe case 8. See U.S. Pat. No. 5,529,070 (Augustine et al.) The accelerometer signals are sampled periodically and, if a predetermined period of time passes without a change in the acceleration signal, the probe can assume that a user is not handling the probe and switch to a hibernate mode. Controls are provided by which the user can switch the probe to hibernate mode manually, in addition to automatic timeouts to the hibernate mode. A combination of the two is to enable the user to set the timeouts to the hibernate mode at lower time durations. This can also be done indirectly by the system. For example, the user can set the remaining period of time that the user would like to perform imaging with the wireless probe. The probe responds to a lengthy required scan period by automatically invoking changes in parameters such as timeouts and transmit beams which are directed to achieving the longer imaging objective.

As shown in FIG. 7, the acquisition module 94 senses the signal from a thermistor near the transducer stack of the probe and also uses a thermometer 212 inside the case to measure the heat developed by other probe components. When either of these temperature-sensing devices indicate an excessive thermal condition, the probe will switch to a low power mode. Several parameters can be altered to achieve a lower power mode of operation. The transmit power of the transducer array can be lowered by decreasing the ±30 volt drive supply for the transducer array. While this measure will reduce heat production, it can also affect the depth penetration and clarity of the image produced. Compensation for this change can be provided by automatically increasing the gain applied to received signals in the host system. Another way to decrease heat production is to lower the clock rate of digital components in the probe. See U.S. Pat. No. 5,142,684 (Perry et al.) Yet another way to reduce heat production and conserve power is to vary imaging parameters. The acquisition frame rate can be reduced, which reduces the amount of transmit power used per unit of time. The spacing between adjacent transmit beams can be increased, producing a less resolved image which can, if desired be improved by other measures such as interpolating intermediate image lines. Another approach is to change the frame duty cycle. A further measure is to reduce the active transmit aperture, receive aperture, or both, thereby reducing the number of transducer elements which must be served with active circuitry. For instance, if a needle is being imaged during a biopsy or other invasive procedure, the aperture can be reduced as high resolution is not required to visualize most needles with ultrasound. Another approach is to reduce the r.f. transmit power, preferably with a message to the user suggesting that the user reduce the spacing between the wireless probe and the host system, if possible, so that high quality images can continue to be produced with reduced r.f. transmit power. A reduction of r.f. transmit power (either acoustic or communication) is preferably accompanied by an increase of the gain applied by the host system to the received r.f. signals.

A difficulty posed by a wireless probe is that it can become separated from its host ultrasound system and more easily lost or stolen than a conventional cabled probe. FIG. 11 illustrates a solution to this problem, which is to use the radiated r.f. field of the wireless probe 10 and/or its host system 40 to locate or track the wireless probe. FIG. 11 illustrates an examination room 300 in which is located an examination table 312 for examining patients with a wireless probe 10. The diagnostic images are viewed on the display screen of a host ultrasound system 40, seen in an overhead view. Two r.f. range patterns 320 and 322 are shown drawn with the wireless probe 10 at their center. The inner range 320 is the preferred range of operating the wireless probe 10 and its host system 40. When the wireless probe and its host system are within this range distance, reception will be at a level providing reliable probe control and low-noise diagnostic images. When the wireless probe and its host system are within this range the signal strength indicator 132 will indicate at or near a maximum strength. However if the wireless probe and its host system become separated by a distance beyond this range, such as outside the preferred range 320 but within the maximum range 322, operation of the wireless probe may become unreliable and consistent high quality live images may not be received by the host. In this circumstance the signal strength indicator will begin to show a low or inadequate signal strength and an audible warning may be issued by the probe beeper 102 or by an audible and/or visual indicator on the host system.

This ability to detect when the wireless probe is within range of the host system may be used for a variety of purposes. For instance, it may be the intention of the medical facility that the wireless probe 10 stay in examination room 300 and not be taken to any other room. In that case, if someone tries to exit the door 302 with the wireless probe 10, the signal strength or timing (range) indicator will detect this travel, and the probe and/or the host system can sound or communicate an alarm, indicating that the wireless probe is being taken outside its authorized area. Such transport may be inadvertent. For example, the wireless probe 10 may be left in the bedding of the examination table 312. Personnel assigned to remove and replace the bedding may not see the wireless probe, and it can become wrapped up in the bedding for transport to the laundry or incinerator. If this happens, the probe can sound its alarm as it is carried out the door 302 and beyond range of its host system 40, thereby alerting facility personnel to the presence of the wireless probe in the bedding.

This same capability can protect the wireless probe from being taken from the facility. For instance, if someone attempts to take the probe out the door 302, down the hallway 304, and through a building exit 306 or 308, a transmitter or receiver 310 with an alarm can detect when the wireless probe is within the signal area 324 of this detector 310. When the probe 10 passes through the signal area 324, the probe beeper 102 can be triggered and the alarm of the detector 310 sounded to alert facility personnel to the attempted removal of the wireless probe. The system of 310 can also log the time and location of the alert so that a record is kept of unauthorized probe movement.

The probe's onboard beeper or loudspeaker 102 can also be used to locate a missing probe. A command signal is wirelessly transmitted which commands the wireless probe to sound its onboard audible tone. Preferably the transmitter has an extended range which covers the entire area in which the wireless probe may be located. Upon receipt of the command the wireless probe produces a sound which alerts persons in the vicinity to the presence of the probe. Probes which have been misplaced or become covered with bedding can be readily found by this technique. The same technique can be used to enable the hospital to locate a specific probe when the clinician wanting it cannot find it.

FIGS. 12 and 13 illustrate several accessories which can be advantageously used with a wireless probe of the present invention. FIG. 12 shows a pair of video display glasses which may be used for a heads-up display with a wireless probe of the present invention. A heads-up display is particularly desirable when a wireless probe is used in surgery. The wireless probe is desirable for surgical imaging because of the absence of the cable, which would otherwise interfere with the surgical field, requiring extensive sterilization and possibly obstructing the surgical procedure. The wireless probe is ideal for freeing the patient and the surgeon from the hazards of the cable. Furthermore, in surgery, an overhead display is often used to display both patient vital signs and the ultrasound image. Thus, the host system can be located out of the way of the procedure with its ultrasound image shown on the overhead display. Prior to making an incision the surgeon may use ultrasound to discern the anatomy below the site of the incision. This requires the surgeon to look down at the surgical site, then up at the ultrasound display in an uncomfortable and disruptive sequence of maneuvers. The heads-up display 410 of FIG. 12 eliminates this discomfort and distraction. The display 410 includes a small projector 412 which projects the ultrasound image onto a surface such as an LCD display screen or, in this example, the lens of video display glasses 414, enabling the surgeon to look at the surgical site while only shifting the eyes slightly to look at the ultrasound image of the anatomy of the patient. The projector 412 can be provided with its own video display glasses or can clip onto the surgeon's own glasses. The projector 412 can be wired to the host system, but preferably communicates wirelessly with the host system, so that a wire from the projector is not needed and does not interfere with the surgical field. Such an image does not have to have a high real time frame rate, as the surgeon will want to look at a relatively stationary ultrasound image in relation to the surgical site. Consequently the bandwidth requirements for communication to the projector 412 can be relatively low. Alternatively, the FPGA 200 of the acquisition module can be programmed to perform scan conversion and the scan converted image transmitted directly from the wireless probe to the wireless heads-up display. A similar ultrasound display can be provided with wrap-around goggles, but since this would prevent the surgeon from easily observing the surgical site while watching the ultrasound image, an imaging technique which permits both to be viewed simultaneously or in rapid succession is preferable.

For procedures such as the foregoing surgical procedure where a surgeon is manipulating surgical instruments at a surgical site and cannot also manipulate ultrasound controls for imaging, voice control of the wireless probe is preferable. FIG. 13 shows a Bluetooth voice transceiver 420 which fits over the ear of a user and includes a microphone 422 by which the user can issue verbal commands to the wireless probe.

Such a voice transceiver can be used with a base station host such as the iU22 ultrasound system produced by Philips Medical Systems of Andover, Mass. which has onboard voice recognition processing. A user can use the wireless voice transceiver 420 to issue verbal commands to control the operation of the iU22 ultrasound system. In accordance with the principles of the present invention, an ultrasound system with voice recognition capability also includes a transceiver for communicating with a wireless probe. Such a host ultrasound system can receive verbal commands from a user, either by a wired microphone or wirelessly using a wireless headset such as that shown in FIG. 13, and through voice recognition convert the verbal commands into command signals for a wireless probe. The command signals are then transmitted wirelessly to the wireless probe to effect the commanded action. For instance, the user could alter the depth of the displayed image by commanding "Deeper" or "Shallower", and the host system and wireless probe would respond by changing the depth of the ultrasound image. In a particular embodiment it may also be desirable to transmit verbal information to the user to indicate that the commanded action was accomplished. Continuing with the foregoing example, the host system could respond with the audible information from a voice synthesizer and loudspeaker that the "Depth changed to ten centimeters." See, for example, U.S. Pat. No. 5,970,457 (Brant et al.) The wireless transceiver of FIG. 13 includes an earpiece 424 which the user can wear in the ear so that audible responses to verbal commands are broadcast directly into the ear of the user, improving comprehension in a noisy environment.

The voice recognition processing could be located in the wireless probe so that the user can communicate commands directly to the wireless probe without going through the host system. However voice recognition processing requires the appropriate software and hardware and, significantly, imposes an additional power requirement on the battery-powered probe. For these reasons it is preferred to locate the voice recognition processing at the host system in which it is readily powered by line voltage. The interpreted commands are then easily transmitted to the wireless probe for implementation. In applications as described above, where a user wants a probe without any user interface devices on the wireless probe, voice control provides a suitable means for controlling the wireless probe.

FIG. 14 illustrates a fully integrated wireless ultrasound system constructed in accordance with the principles of the present invention. At the center of the system is a host system 40, 50, 60 which is programmed for pairing with a number of wireless ultrasound imaging devices and accessories. (The symbol labeled 2 indicates a wireless communication link.) Foremost is a wireless probe 10 which responds to command signals and communicates image data to the host system 40, 50, 60. The host system displays the ultrasound image on its system display 46, 56, 66. Alternatively or additionally, the image is sent to a heads-up display 410 where the ultrasound image is displayed for more convenient use by a user. The wireless probe 10 is controlled by a user interface located on the probe itself as shown in FIGS. 9a and 9b. Alternatively or additionally the controls for the wireless probe may be located on the host system 40, 50, 60. Yet another option is to use a wireless user interface 32 which communicates control commands directly to the wireless probe 10 or to the host system for relay to the wireless probe. Another option is a footswitch control. Still a further option is to control the probe verbally by words spoken into a microphone 420. These command words are transmitted to the host system 40, 50, 60 where they are recognized and converted into command signals for the probe. The command signals are then sent wirelessly to the probe 10 to control the operation of the wireless probe.

What is claimed is:

1. A wireless ultrasound probe which transmits image data wirelessly to a host system comprising:
    an array transducer;
    an acquisition circuit coupled to the array transducer;
    a transceiver coupled to the acquisition circuit which acts to wirelessly exchange r.f. image data signals with the host system;
    a battery which operates to provide energizing potential to the array transducer, the acquisition circuit, and the transceiver;
    a probe case housing the array transducer, acquisition circuit, transceiver and battery;
    a range indicator based on r.f. signal reception; and
    a loudspeaker responsive to indicated signal strength which acts to issue an audible tone in response to reception of signals of an undesired signal strength,
    wherein the r.f. signal strength is a function of the range between the wireless probe and the host system, and wherein the range comprises:
    a near field range in which the loudspeaker is not sounded due to the range;
    an intermediate field range in which the loudspeaker is sounded due to the range; and
    a far field range in which the wireless probe and the host system are unable to effectively communicate with each other.

2. The wireless ultrasound probe of claim 1, wherein the loudspeaker is sounded when the range between the wireless probe and the host system is the far field range.

* * * * *